United States Patent [19]

Ohta et al.

[11] Patent Number: 5,339,811
[45] Date of Patent: Aug. 23, 1994

[54] MAGNETOENCEPHALOGRAPH

[75] Inventors: Hiroshi Ohta, Tokyo; Kazutomo Hoshino, Ageo, both of Japan

[73] Assignees: Mitsui Mining & Smelting Co., Ltd., Tokyo; The Institute of Physical and Chemical Research (Riken), Saitama, both of Japan

[21] Appl. No.: 969,489

[22] Filed: Oct. 30, 1992

[30] Foreign Application Priority Data

Nov. 6, 1991 [JP] Japan ................... 3-318354

[51] Int. Cl.$^5$ ............................................. A61B 5/05
[52] U.S. Cl. ............................ 128/653.1; 324/244; 324/248; 324/249
[58] Field of Search ............ 128/653.1; 324/244, 324/248, 249

[56] References Cited

U.S. PATENT DOCUMENTS

| | | | |
|---|---|---|---|
| 3,557,777 | 1/1971 | Cohen | 128/653.1 |
| 4,613,817 | 9/1986 | Hoenig | 324/248 |
| 4,913,152 | 4/1990 | Ko et al. | 128/653.1 |
| 4,996,479 | 2/1991 | Hoenig | 128/653.1 X |
| 5,136,242 | 8/1992 | Abraham-Fuchs | 324/244 |
| 5,142,229 | 8/1992 | Marsden | 324/248 |
| 5,152,288 | 10/1992 | Hoenig et al. | 324/248 X |
| 5,158,932 | 10/1992 | Hinshaw et al. | 324/248 |
| 5,187,327 | 2/1993 | Ohta et al. | 174/35 R |
| 5,193,348 | 3/1993 | Schnapper | 324/248 |
| 5,265,609 | 11/1993 | Buchanan et al. | 324/248 |
| 5,265,611 | 11/1993 | Hoenig et al. | 324/248 |

FOREIGN PATENT DOCUMENTS 0406963  1/1991  European Pat. Off. ......... 128/653.1

OTHER PUBLICATIONS

Clark, SQUIDS, Brains, and Gravity waves, Physics Today, Mar. 1986, pp. 36-44.

*Primary Examiner*—Lee S. Cohen
*Assistant Examiner*—Brian L. Casler
*Attorney, Agent, or Firm*—Flynn, Thiel, Boutell & Tanis

[57] ABSTRACT

A magnetoencephalograph comprising an oxide superconductor magnetic shielded vessel and a cryostat for cooling the magnetic shielded vessel, a multichannel SQUID and a cryostat for cooling the SQUID inserted together in the magnetic shielded vessel from one end of the magnetic shielded vessel, a magnetic-field detection unit situated in the vessel for detecting magnetic fields, and a coupling portion for coupling the SQUID and the magnetic-field detection unit with respect to the signals, and the SQUID and the magnetic-field detection unit being detachable. The magnetoencephalograph makes possible the detection of the very weak magnetic fields from the human brain and therewith reduction of the diameter of the opening of the magnetic shield vessel for inserting the SQUID. The reduction of the diameter of the SQUID opening in turn makes it possible to reduce the length of the magnetic shielded vessel, thereby preserving a high shielding effect of the magnetic shield vessel because of the L/D relationship. The magnetic shielded vessel is thus reduced to a practical size which is easy to handle and fabricatable at a low cost.

9 Claims, 5 Drawing Sheets

MAGNETOENCEPHALOGRAPH

BACKGROUND OF THE INVENTION a) Field of the Invention

This invention relates to a magnetoencephalograph for detecting the very weak magnetic fields from human brain using a high sensitivity SQUID (Superconducting Quantum Interference Devices), and more particularly to a magnetoencephalograph which uses an oxide superconductor magnetic shielded vessel which repels magnetic fluxes by a phenomenon of superconductivity of Meissner effect to exclude outside noises and thereby make it possible to detect the very weak magnetic fields from different parts of the brain and preferably has a magnetic-field detection unit comprising a plurality of gradiometers or magnetometers arranged in a helmet-shaped configuration fitting over the head.

b) Description of the Prior Art

Recently, researches attempting to elucidate the brain mechanism or the causes of headache or to make possible the medical examination of the brain by measuring magnetic fields from the brain have become active. Though imaging of the inside of the brain by X-ray CT (Computed Tomography), MRI (Magnetic Resonance Imaging) and PECT (Positron Emission Computed Tomography) are used in clinical examinations, there are various problems in the resolution of images, the response time, the limit of the X-rays used, and the exposure of patients to X-rays. EEG (Electoencephalography) is another method of examining the inside of the brain and is widely used in the clinical examination, but this method also has problems in that the electrodes must be stuck on the surface of the head and that the signals are distorted by the cranial bones. On the other hand, MEG (Magnetoencephalography), a method of making a map of the magnetic field distribution on the surface of the brain, has great advantages that measurements can be conducted without contact leads and that this method is effective not only for locating diseased parts in the brain but also for elucidating the functions of the brain for its quick response. Since the magnetic fields from the brain, however, are as weak as $10^{-12}$ to $10^{-15}$ (Tesla) and in a very low frequency region of 0.1 to 10 Hz, a conventional magnetic shield using a ferromagnetic material is not effective enough to detect the signals. The inventors of this application have experimentally confirmed before that a magnetic shield using an oxide superconductor is effective for biomagnetic measurements (JAPANESE JOURNAL OF APPLIED PHYSICS, VOLUME 28, NO. 5, 1989, L813 and volume 29, No. 8, 1990, L1435).

In order to locate diseased parts in the brain by measurements of the magnetic fields from the brain, the magnetic field distribution of the brain must be known by detecting the magnetic fields from different parts of the brain by means of a multichanneled SQUID. To conduct such measurements in a superconducting magnetic shielded vessel, a very large superconducting magnetic shielded vessel capable of housing a cryostat to cool the SQUID fluxmeter must be fabricated, and the superconducting magnetic shielded vessel itself must be cooled in a cryostat. Fabrication of such a large vessel, if technically possible, is attended with much difficulty and a high cost. Further, if many detecting elements are arranged so as to cover the head and detect the magnetic fields in all directions, the magnetic-field detection unit becomes considerably large in diameter. Moreover, since the SQUID must be replaced frequently because of its unstable characteristic, the superconducting magnetic shielded vessel must have a large opening formed in the top end to insert the SQUID in or retract it from the vessel, if the SQUID and the magnetic-field detection unit are constructed in a single unit. Such a large SQUID opening allows external magnetic fields to creep deeper into the vessel and so a much longer magnetic shielded vessel is required, consequently causing a problem of increase of the size of the magnetic shielded vessel.

SUMMARY OF THE INVENTION

An object of the present invention is to provide a magnetoencephalograph which uses a conventional multichannel SQUID fluxmeter without modification and the SQUID being insertable in and retractable from the magnetic shielded vessel, with the larger-diameter, helmet-shaped, magnetic-field detection unit situated in the magnetic shielded vessel by detachably coupling the SQUID and the magnetic-field detection unit by means of a coupling portion for coupling them electromagnetically.

Another object of the present invention is to provide a magnetoencephalograph whose magnetic shielded vessel is of a practical size, easy to handle, fabricatable at a low cost and with a small height, which is realized by reduction of the SQUID opening and made possible by the above construction and the resultant shallower flux creep from the smaller SQUID opening.

The other objects of the present invention will become clear by the following description.

Provided by the present invention is a magnetoencephalograph which comprises an oxide superconductor magnetic shielded vessel and a cryostat for cooling the magnetic shielded vessel, a multichannel SQUID and a cryostat for cooling the SQUID inserted together in the magnetic shielded vessel from above the top end of the magnetic shielded vessel, a magnetic-field detection unit situated in the magnetic shielded vessel for detecting magnetic fields, and a coupling portion for coupling the SQUID and the magnetic-field detection unit with respect to the signals, the SQUID and the magnetic-field detection unit being detachable, and thereby can detect the very weak magnetic fields from human brains ($10^{-12}$ to $10^{-15}$T) stably at a high S/N ratio.

The oxide superconductor magnetic shielded vessel of the present invention is operational at the liquid nitrogen temperature, is a cylindrical or polygonal hollow cylinder, and has an opening for inserting the human body and a much smaller SQUID opening for inserting the SQUID.

Further, the magnetic-field detection unit comprises a plurality of gradiometers or magnetometers, the gradiometers or magnetometers preferably being arranged in a helmet-shaped configuration fitting over the head, and the gradiometers or magnetometers being formed by applying an oxide superconductor paste or vapor-depositing Nb films on the surface of a substrate or by winding a Nb wire about a substrate.

DETAILED DESCRIPTION OF THE PREFERRED EMBODIMENTS

Next described are preferred embodiments of the magnetoencephalograph of the present invention with reference to the accompanying drawings, but it should be understood that the present invention is not limited to those embodiments.

Figure 1:
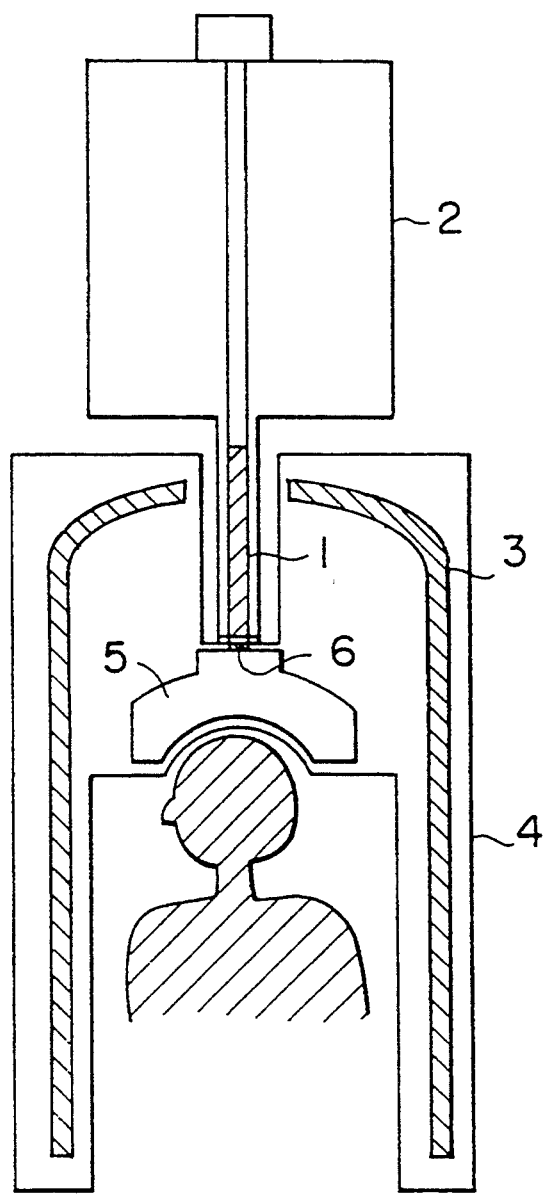
FIG. 1 is a schematic sectional view of an embodiment of the magnetoencephalograph of the present invention.

The magnetoencephalograph of the present invention, as shown in FIG. 1, comprises an oxide superconductor magnetic shielded vessel 3 and a cryostat 4 for cooling the vessel 3, a multichannel SQUID 1 and a cryostat 2 for cooling the SQUID inserted together in the vessel 3 from above the top end of the magnetic shielded vessel 3, a magnetic-field detection unit 5 for detecting magnetic fields, and a coupling portion 6 for detachably coupling the SQUID 1 and the magnetic-field detection unit 5 with respect to the signal contained in the vessel 3.

The SQUID 1 is the type which utilizes a quasi-planar Josephson junction of Nb thin films currently being put to practical use, for example. The device operates at the liquid helium temperature. A multichannel SQUID currently being put to practical use has 7 channels and the number of the channels is increasing. When using a multichannel SQUID and arranging the corresponding number of detecting elements in a helmet-shaped configuration covering the whole head and constructing them in a single unit, the diameter of the bottom end portion of the cryostat 2 becomes considerably large, 70 cm for example, to house the magnetic-field detector.

The magnetic shielding effect at a position in an oxide superconductor magnetic shield vessel in a circular or polygonal hollow cylinder is determined by the ratio of the distance (L) from an opening to the place to the diameter of the opening (D) L/D (refer to the aforementioned papers). It is required to make the magnetic shielded vessel smaller in diameter and larger in height also from the point of cost reduction and convenience in practical use. For the magnetic shielded vessel shown in FIG. 1, 1 m in diameter at the cylindrical portion and 20 cm in the diameter of the SQUID opening, for example, L/D must be equal to or greater than 1 (theoretical attenuation ratio is 1/1000 or smaller). To make L/D at the measuring position equal to 1 for the magnetic shield vessel of the shape as shown in FIG. 1, the sum of the distance from the bottom opening for a patient (1 m×1=1 m) and that from the SQUID opening (20 cm×1=20 cm) at the top end is 1.2 m. The magnetic shielded vessel of this height is small enough for the apparatus to be installed in a usual electromagnetic-shielded room or laboratory. Further, the SQUID and the magnetic-field detection unit are indirectly coupled (inductive coupling) and detachable, which makes maintenance and replacement of the SQUID very easy. If the magnetic-field detection unit is housed in the bottom end portion of the cryostat 2 and inserted in the magnetic shielded vessel through a larger opening, the distance from the top end to the measuring position must be 70 cm in order to make L/D equal to 1: the height of the vessel then becomes 1.7 m. Moreover, to make L/D greater than 1, the size of the magnetic shielded vessel becomes even more larger, which causes great difficulty in fabrication and an increase in its cost.

Figure 2:
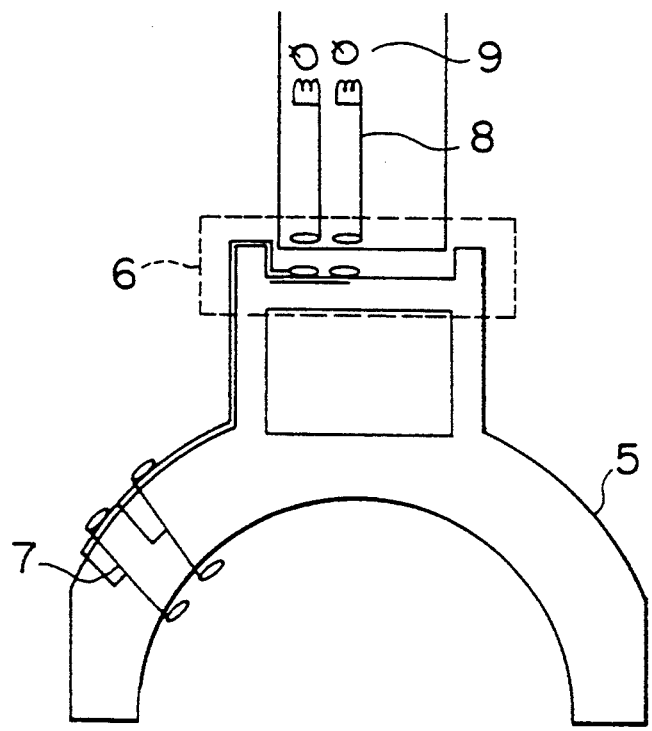
FIG. 2 is a schematic diagram of an embodiment of the magnetic-field detection and amplification unit.

Described below is the magnetic-field detection unit 5 of the present invention. The magnetic-field detection unit 5, as shown in FIG. 2, comprises many first-order differential gradiometers 7 with their detecting portions arranged so as to closely fit over the head. The signal detected by each gradiometer 7 is transmitted through the indirect coupling (inductive coupling) from its coupling portion 6 to the coupling portion 8 of each SQUID element 9 and then to each SQUID element 9.

Figure 3:
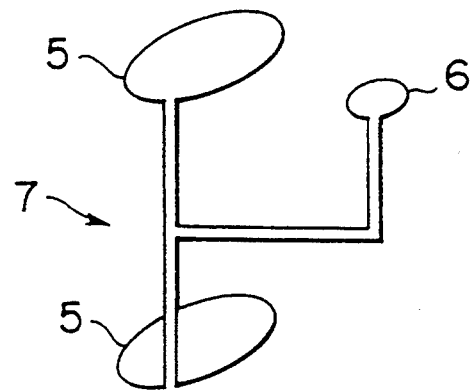
FIG. 3 is a schematic diagram of a first-order differential gradiometer.

The gradiometers 7 can be formed in such a configuration that the loops of their magnetic-field detecting portion are greater in area than the loop of their coupling portion inductively coupled with the SQUID and signals detected are amplified, as shown in FIG. 3.

Figure 4:
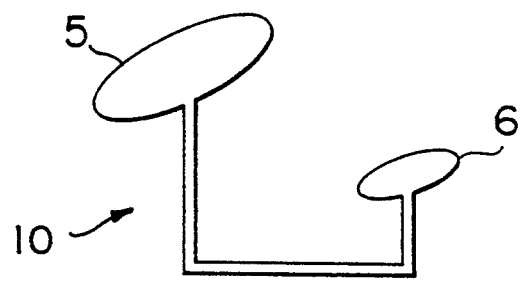
FIG. 4 is a schematic diagram of a magnetometer.

For the magnetoencephalograph of the present invention, as gradiometer 7 of the first-order differential type may be replaced by a magnetometer 10 of the simpler configuration as shown in FIG. 4 which detects the signal from a subject as it is. By the use of the magnetometer 10 instead of the gradiometer 7, detection of the signals from the deeper regions in the brain is made possible.

The gradiometers 7 or magnetometers 10 can be formed by depositing an oxide superconductor which is operational at the liquid nitrogen temperature on the surface of a substrate by silkscreening or drawing and then sintering the material, for example. FIG. 2 shows a configuration of the magnetic-field detection unit 5 for use at the liquid nitrogen temperature. When it is difficult to form a plurality of the gradiometers or magnetometers on a single substrate, the magnetic-field detection unit 5 may be fabricated by forming each gradiometer or magnetometer on a magnesia substrate separately and assembling them in a helmet-shaped configuration.

Figure 5:
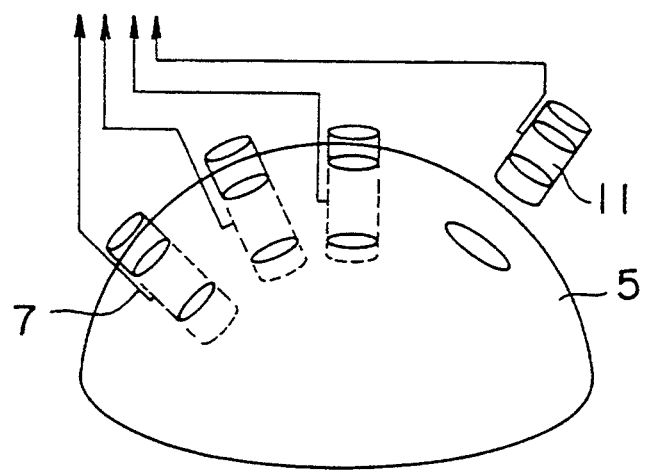
FIG. 5 is a schematic diagram of the first-order differential gradiometers arranged in a helmet-shaped configuration.
Figure 6:
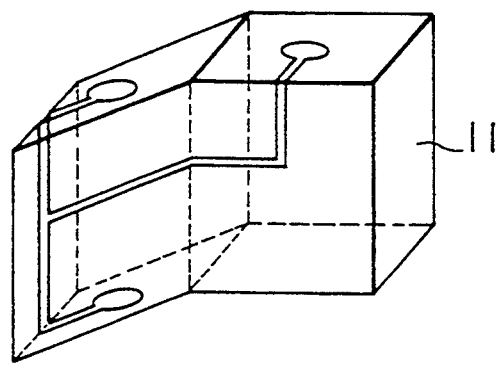
FIG. 6 is a gradiometer formed by applying an oxide superconductor paste on the surface a substrate.

The gradiometers 7 shown in FIG. 5 are made by winding a conventional Nb wire used at the liquid helium temperature about a cylindrical substrate 11, and arranged in a helmet-shaped configuration. The wires from each gradiometer 7 can be directly and detachably connected to those from each SQUID element by means of a Nb connector (superconductive coupling). Each gradiometer 7 can also be made by applying an oxide superconductor paste on the surface of a magnesia substrate 11 and sintering the paste as shown in FIG. 6.

Figure 7:
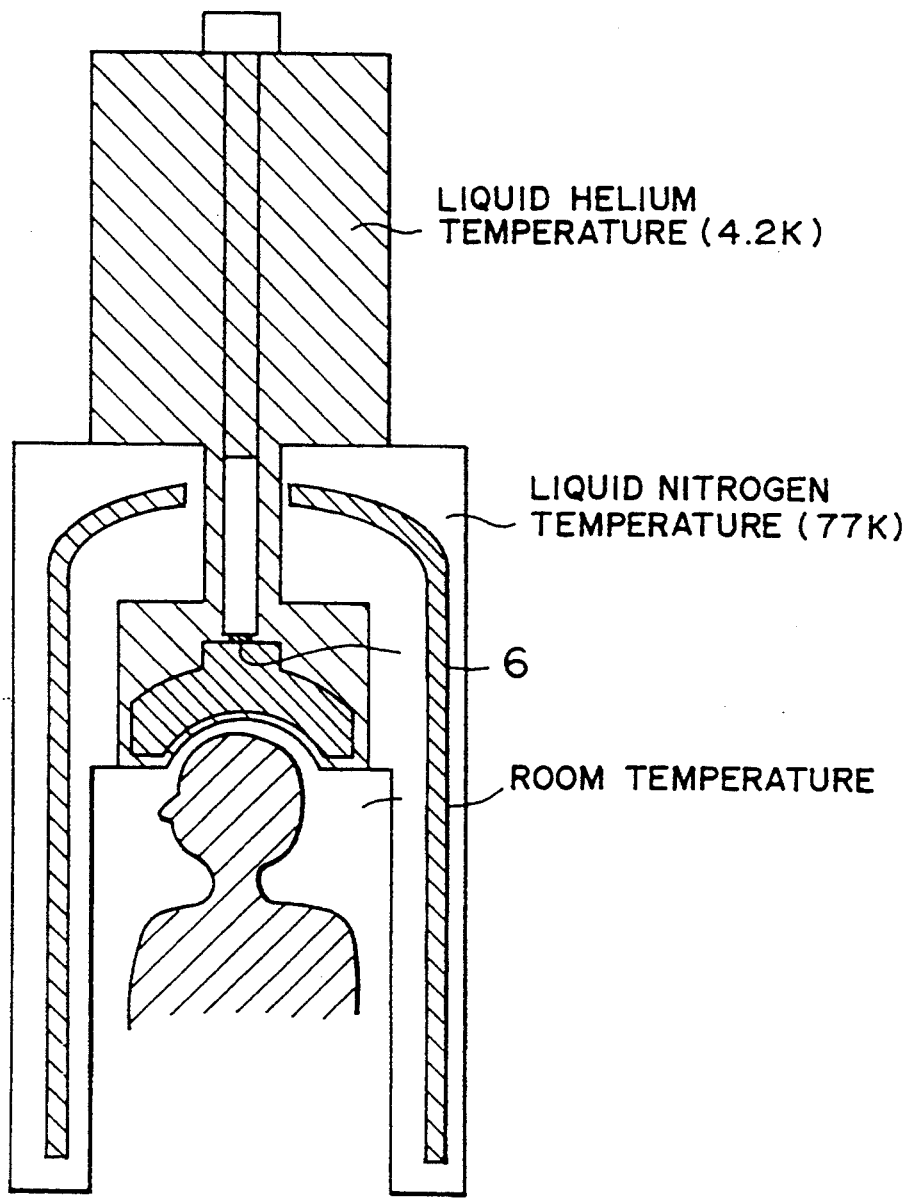
FIG. 7 is a schematic sectional view of an embodiment of the apparatus with a magnetic-field detection unit at the liquid helium temperature.

The magnetic-field detection unit 5 may be operational either at the liquid nitrogen temperature or at the liquid helium temperature. For both temperatures, the SQUID which is 1 and the magnetic-field detection unit 5 using gradiometers 7 or magnetometers 10 can be detachably coupled by the coupling portion 6. FIG. 7 shows an embodiment of the magnetoencephalograph of the present invention having a magnetic-field detection unit operational at the liquid helium temperature.

The construction of the magnetoencephalograph of the present invention can also be used without modification when a SQUID operational at the liquid nitrogen temperature is put to practical use in the future.

For the superconductor for the magnetic shielded vessel 3, both yttrium-system and bismuth-system superconductors are usable, but bismuth-system superconductors are preferable for their smaller change of properties over time and higher superconductivity critical temperature. The vessel 3 can be fabricated by powder sintering or thick film formation over a metal or ceramic substrate.

Though the cooling system of the SQUID, magnetic-field detection unit and magnetic shielded vessel is divided into two separate systems, the cryostat 2 for cooling the SQUID and the cryostat 4 for cooling the magnetic shielded vessel and magnetic-field detection unit, as in the embodiment shown in FIG. 1, it may be a single system. Further, the construction of the cooling system can be appropriately modified according to the temperature at which the apparatus is used, that is, the liquid helium temperature or the liquid nitrogen temperature.

Constructed as described above, the magnetoencephalograph of the present invention can detect very weak magnetic fields from the human brain stably at a high S/N ratio and has the following effects:

(1) The separation and detachable coupling of the SQUID and the magnetic-field detection unit make it possible to reduce the diameter of the opening in one end of the vessel through which the coupling portion of the SQUID is inserted. The smaller diameter of the SQUID opening in turn permits the reduction of the length of the magnetic shielded vessel without deteriorating the magnetic-shielding effect because of the L/D relationship. As a result, the magnetic shielded vessel of the present invention is reduced to a practical size easy to handle and fabricatable at a low cost.

(2) The magnetic-field detection unit comprising a plurality of gradiometers arranged in a helmet-shaped configuration, in combination with a multichannel SQUID, makes possible the simultaneous detection of the magnetic fields from different parts of the brain.

(3) The tightly magnetic-shielded space ($10^{-6}$ or smaller attenuation ratio, for example) in which the magnetic-field detection unit is situated makes it possible to detect very weak magnetic fields.

(4) The separation and detachable coupling of the SQUID and the magnetic-field detection unit also makes the handling and maintenance of the SQUID very easy.

Next described are specific embodiments of the present invention.

EXAMPLE 1

Bi—Pb—Sr—Ca—Cu—O powder with a molar ratio of Bi:Pb:Sr:Ca:Cu=0.8:0.4:0.8:1.0:1.4 was synthesized by the ethanol-aided coprecipitation method with oxalic acid. The powder was suction-filtered, dried in two stages at 100° C. and 500° C., calcined at 790° C. for 24 h, and ground. The resultant powder was pressed, annealed at 845° C. for 24 h, and ground again. This pressing, calcining and grinding process was repeated three times. Most particles of the powder thus obtained were confirmed to be in the Bi-system 110K phase by X-ray analysis. The powder was then pressed into a hollow cylindrical vessel with one end open by means of a cold isostatic press. The vessel was 32 cm in diameter at the open end and 64 cm in depth. An opening of 18 cm in diameter was made in the closed end. The vessel was then heated at 845° C. for 48 h. Thus a superconducting magnetic shielded vessel was fabricated.

A cryostat as shown in FIG. 1 was made so as to cool the magnetic shielded vessel with liquid nitrogen. The inside outer wall of the cryostat was aluminum and the outside outer wall stainless steel, and the liquid nitrogen vessel in which the magnetic shielded vessel was housed and cooled down to the liquid nitrogen temperature was isolated from the outer walls by a vacuum heat-insulating space.

The shielding effect of the vessel was measured to be about $10^{-6}$ in attenuation rate. There was a good agreement between the shielding effect measured and that expected theoretically from the L/D relationship.

For simplification, a gradiometer as shown in FIG. 6 was made for detection of magnetic fields by applying an oxide superconductor powder on the surface of a magnesia substrate. The diameters of the detecting portion of the gradiometer were 30 mm, the inductive coupling portion was a circular loop of 25 mm in diameter, and the line width was 1 mm. The superconductor paste was prepared by adding 3 Wt % of an acrylic resin and a few drops of terpineol (as a solvent) and di-n-butylphthalate (as a plasticizer) to 10 Wt % of the superconductor powder described above and kneading them well. Then, the figure of the gradiometer was drawn on the surface of the substrate, the regions of the surface at both sides of the lines were covered with adhesive tape, and the paste was applied over the lines. The SQUID used was a 1-channel, quasi planer, RF-SQUID using niobium films. Liquid nitrogen was filled into the cryostat, and the magnetic shielded vessel was cooled slowly spending about 24 h, while canceling the magnetic field of the earth with a Helmholtz coil of about 1.5 m in diameter in order to prevent the magnetic field of the earth from being trapped inside the superconducting magnetic shielded vessel. Liquid helium was filled into the SQUID-cooling cryostat to make the SQUID operational, and the SQUID was inserted into the magnetic shielded vessel through the SQUID opening. The distance between the coupling coil in the coupling portion of the SQUID and that of the gradiometer shown in FIG. 2 was about 2 cm, and both coils could be coupled accurately.

An one-turn coil of 30 mm in diameter, made of copper wire, was placed at the position in the magnetic shielded vessel to where the head was inserted (just below the xgradiometer) and an alternating current was applied to the coil so as to generate a magnetic field of 5 Hz and $10^{-12}$ T. This weak magnetic field was detected by a FFT (Fast Fourier Transform) analyzer connected to the SQUID. It was confirmed that such a very weak magnetic field can be detected at a sufficiently high S/N ratio and that measurement of the magnetic fields from the brain is feasible in practice by the magnetoencephalograph of the present invention.

EXAMPLE 2

Figure 8:
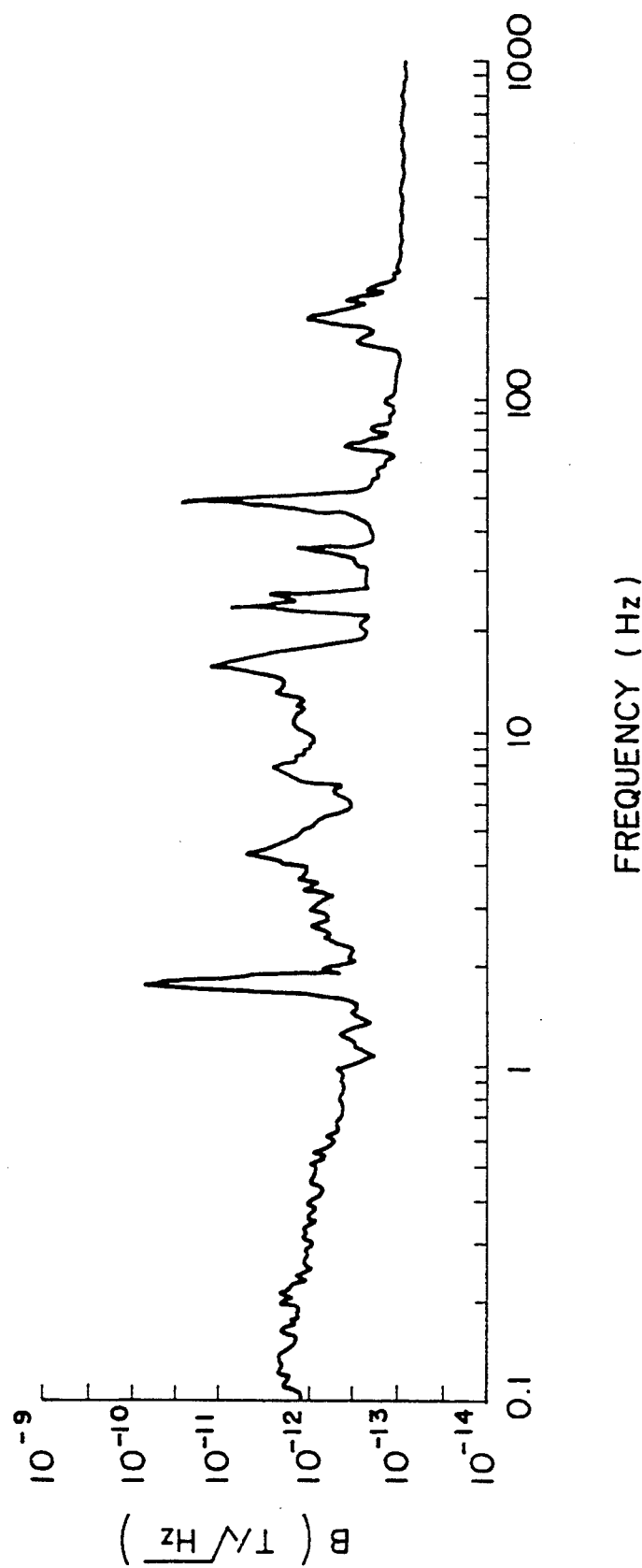
FIG. 8 is the noise spectrum in the vessel of the embodiment of FIG. 2.

A magnetometer of 25 mm in diameter was made of 0.1 mm Nb superconductor wire. The cryostat for cooling the SQUID and that for cooling the magnetic shielded vessel were constructed in a single unit so as to cool the magnetometer and the magnetic shielded vessel with liquid helium. The magnetometer was put in the cryostat and connected to the terminals of the wires from the SQUID by means of a Nb connector. Then the same measurements as those of Example 1 were conducted. The noise spectrum in the magnetic shielded vessel obtained by measurement is shown in FIG. 8. As known from FIG. 8, the noise level in the magnetic shielded vessel is very low. The shielding characteristic does not deteriorate even in the low frequency range below 10 Hz. Thus it was confirmed that very weak magnetic fields below $10^{-12}$ can be detected.

What is claimed is:

1. A magnetoencephalograph comprising an oxide superconductor magnetic shielded vessel, a cryostat housing the vessel for cooling the magnetic shielded vessel, a multichannel SQUID, a cryostat housing the SQUID for cooling the SQUID, a magnetic field detection unit and a coupling portion indirectly coupling the SQUID and the magnetic field detection unit, the SQUID, a portion of the cryostat for cooling the SQUID, the magnetic field detection unit and the coupling portion being contained in the magnetic shielded vessel, the SQUID and a portion of the cryostat for cooling the SQUID being inserted together in the magnetic shielded vessel through a top end thereof and the SQUID and the magnetic field detection unit being detachable from each other.

2. The magnetoencephalograph of claim 1, wherein said oxide superconductor magnetic shielded vessel is operational at a liquid nitrogen temperature and is a circular or polygonal hollow cylinder with an opening for inserting a human body at a bottom end and an opening for inserting the SQUID at the top end, said opening for inserting the SQUID being smaller in diameter than said opening for inserting the human body.

3. The magnetoencephalograph of claim 1, wherein said magnetic field detection unit comprises gradiometers or magnetometers.

4. The magnetoencephalograph of claim 3, wherein detecting elements of said magnetic field detection unit are arranged in a helmet-shaped configuration adapted for covering the head of a patient.

5. The magnetoencephalograph of claim 4, wherein said gradiometers or magnetometers are formed by applying an oxide superconductor on a surface of a substrate in a configuration and then sintering the oxide superconductor.

6. The magnetoencephalograph of claim 4, wherein said gradiometers or magnetometers are formed by winding a Nb superconductor wire about a substrate.

7. The magnetoencephalograph of claim 4, wherein said gradiometers or magnetometers are made by forming a thin Nb superconductor film on a surface of a substrate.

8. The magnetoencephalograph of claim 1, wherein the oxide superconductor for the magnetic shielded vessel is a bismuth-system superconductor or a yttrium system superconductor.

9. The magnetoencephalograph of claim 1, wherein the cryostat for cooling the SQUID and the cryostat for cooling the magnetic shielded vessel are a single system.

* * * * *